US007003354B2

(12) United States Patent
Chow et al.

(10) Patent No.: US 7,003,354 B2
(45) Date of Patent: *Feb. 21, 2006

(54) ARTIFICIAL RETINA DEVICE WITH STIMULATING AND GROUND RETURN ELECTRODES DISPOSED ON OPPOSITE SIDES OF THE NEURORETINA AND METHOD OF ATTACHMENT

(75) Inventors: Alan Y. Chow, Wheaton, IL (US); Vincent Y. Chow, Hanover Park, IL (US)

(73) Assignee: Optobionics Corporation, Wheaton, IL (US)

(*) Notice: Subject to any disclaimer, the term of this patent is extended or adjusted under 35 U.S.C. 154(b) by 526 days.

This patent is subject to a terminal disclaimer.

(21) Appl. No.: 10/142,277

(22) Filed: May 9, 2002

(65) Prior Publication Data

US 2002/0169486 A1 Nov. 14, 2002

Related U.S. Application Data

(63) Continuation of application No. 09/564,841, filed on May 4, 2000, now Pat. No. 6,427,087.

(51) Int. Cl.
*A61N 1/18* (2006.01)
(52) U.S. Cl. ........................ 607/54; 623/6.63
(58) Field of Classification Search .......... 607/53, 607/54; 623/6.63
See application file for complete search history.

(56) References Cited

U.S. PATENT DOCUMENTS 3,594,823 A 7/1971 Collins (Continued)

FOREIGN PATENT DOCUMENTS

DE OS 195 29 371 2/1997

(Continued)

OTHER PUBLICATIONS

Article published in *Science News*, Feb. 2, 1974, vol. 105, No. 5, p. 105.

(Continued)

*Primary Examiner*—Jeffrey R. Jastrzab
*Assistant Examiner*—Alyssa M. Alter
(74) *Attorney, Agent, or Firm*—Brinks Hofer Gilson & Lione (57) ABSTRACT

An artificial retinal device, implanted in the subretinal space of the eye in persons with certain types of retinal blindness, induces artificial vision by electrical stimulation of the remaining viable cells of the retina. The artificial retina device includes a stimulating electrode unit preferably placed in the subretinal space, and a tail-like extension housing a distant electrical return ground electrode unit that may be placed in the vitreous cavity. The stimulating electrode unit includes an array of electrode subunits. Each electrode subunit includes one or more microphotodiodes electrically connected, for example, in series to provide increased voltage and current to its microelectrode. The stimulating electrode unit and the ground return electrode of the ground return electrode unit are preferably disposed on opposite sides of the neuroretina to allow for efficient and high resolution transretinal electrical stimulation of the neuroretinal cells. Additional photodiodes may be incorporated into the circuitry of the artificial retina device to provide additional bias voltage and current to the microelectrode subunits of the stimulating electrode unit. In another preferred embodiment, the ground return electrode in the tail-like extension is disposed in the capsular bag of the eye, after lens nucleus and cortex removal, where it is electrically connected to an additional bias photodiode or photodiodes.

52 Claims, 11 Drawing Sheets

U.S. PATENT DOCUMENTS

| | | | |
|---|---|---|---|
| 3,628,193 | A | 12/1971 | Collins |
| 3,766,311 | A | 10/1973 | Boll |
| 3,848,608 | A | 11/1974 | Leonard |
| 3,914,800 | A | 10/1975 | Collins |
| 4,001,867 | A | 1/1977 | Kravitz et al. |
| 4,211,474 | A | 7/1980 | Le Goff |
| 4,251,887 | A | 2/1981 | Anis |
| 4,272,910 | A | 6/1981 | Danz |
| 4,551,149 | A | 11/1985 | Sciarra |
| 4,600,004 | A | 7/1986 | Lopez et al. |
| 4,601,545 | A | 7/1986 | Kern |
| 4,628,933 | A * | 12/1986 | Michelson ............... 607/53 |
| 4,679,572 | A | 7/1987 | Baker, Jr. |
| 4,750,498 | A | 6/1988 | Graham |
| 4,810,050 | A | 3/1989 | Hooper |
| 4,832,202 | A | 5/1989 | Newman et al. |
| 4,873,448 | A | 10/1989 | Shirai |
| 4,978,842 | A | 12/1990 | Hinton et al. |
| 5,016,633 | A | 5/1991 | Chow |
| 5,024,223 | A | 6/1991 | Chow |
| 5,109,844 | A | 5/1992 | de Juan, Jr. et al. |
| 5,130,528 | A | 7/1992 | Phillips, Jr. |
| 5,130,776 | A | 7/1992 | Popovic et al. |
| 5,159,927 | A | 11/1992 | Schmid |
| 5,223,728 | A | 6/1993 | Gempe |
| 5,256,882 | A | 10/1993 | Miyasaka |
| 5,338,991 | A | 8/1994 | Lu |
| 5,351,309 | A | 9/1994 | Lee et al. |
| 5,397,350 | A | 3/1995 | Chow et al. |
| 5,411,540 | A | 5/1995 | Edell et al. |
| 5,476,494 | A | 12/1995 | Edell et al. |
| 5,491,349 | A | 2/1996 | Komoto et al. |
| 5,556,423 | A | 9/1996 | Chow et al. |
| 5,648,655 | A | 7/1997 | Rostoker |
| 5,717,201 | A | 2/1998 | Lin et al. |
| 5,895,415 | A * | 4/1999 | Chow et al. ............... 607/54 |
| 6,230,057 | B1 | 5/2001 | Chow et al. |
| 2003/0139784 | A1 | 7/2003 | Morimoto et al. |

FOREIGN PATENT DOCUMENTS

| | | |
|---|---|---|
| EP | 0 084 621 A2 | 11/1982 |
| EP | 0 233 789 | 2/1987 |
| EP | 0 325 201 A2 | 7/1989 |
| EP | 0 501 904 A2 | 2/1992 |
| GB | 2 229 543 A | 9/1990 |
| JP | A 8-154897 | 6/1996 |
| JP | A 9-266954 | 10/1997 |
| JP | A 2000-24122 | 1/2000 |

OTHER PUBLICATIONS

Article published in *Science*, Jul. 1981.
Abrams, Dr. Susan B., "Implanted photodiodes could restore lost vision", Biophotonics Research, 2 pages, 1997.
Ando, Haruhisa, et al. "Design Consideration and Performance of a New MOS Imaging Device", 6 pages, IEEE (1985).
Armington, J.C., Brigell, M., "Effects of Stimulus Location and Pattern Upon the Visually Evoked Cortical Potential and the Electroretinogram," *Int J. Neurosci*, 1981; 14:169-178.
Baylor, D.A., Fourtes, M.G.F., "Electrical Responses of Single Cones in the Retina of the Turtle," *J Physiol*, 1970; 207:77-92.
Bergmann-Schaefer, "Lehrbuch der Experimentalphysik" (Textbook of Experimental Physics), vol. II, "Electricity and Magnetism" by Prof. Dr. -Ing. H. Gobrecht, 3 pp., (1971) plus translation.
Bobsch, M.D., Joseph M. and Grosser, Ph.D., Morton "Newer Repair at the AXOM Level: A Merger of Microsurgery and Microelectronics," VCH Publishers, Inc. (1967).
Boettner, E.A., Wolter, J.R., "Transmission of the Ocular Media," *Invest Ophthalmol*, 1962; 1:776-783.
Brady, G.S., Clauser, H.R., *Materials Handbook, Thirteenth Edition*, New York, McGraw-Hill, 1991; 739-740.
Brindley, G.S., "The Site of Electrical Excitation of the Human Eye," *J. Physiol*, 1955; 127-189-200.
Brindley, G.S., "Beats Produced by Simultaneous Stimulation of the Human Eye with Intermittent Light and Intermittent or Alternating Electric Current," *J. Physiol*, 1962; 164:156-167.
Brown, et al., "Monolithically Integrated 1×12 Array of Planar InGaAs/InP Photodiodes," *Journal of Lightwave Technology*, vol. LT-4, No. 3, Mar. 1986, pp. 283-286.
Chapin, D.M., et al., "A New Silicon *p-n* Junction Photocell for Converting Solar Radiation into Electrical Power," Letters to the Editor, Journal of Applied Physics, vol. 25, (Jan.-Dec., 1954).
Chow, A.Y., "Electrical Stimulation of the Rabbit Retina with Subretinal Electrodes and High Density Microphotodiode Array Implants," ARVO Abstracts, *Invest Ophthalmol Vis Sci*. 199334 (Suppl):835.
Curcio, C.A., Sloan, K.R., Kaliha, R.E., Hendrickson, A.E., "Human Photoreceptor Topography," *J of Comparative Neurology*, 1990; 292:497-523.
Dawson, W.W., Radtke, N.D., "The Electrical Stimulation of the Retina by Indwelling electrodes," *Invest Ophthalmol Vis Sci.*, 1997; 16:249-252.
Dowling, J.E., Ripps, H., Visual Adaptation in the Retina of the Skate, *J Gen Physiol*, 1970; 56:491-520.
Eagle, R.C., Lucier, A.C., Bernardino, V.B., et al., "Retinal Pigment Epithelial Abnormalities in Fundus Flavimaculatus," *Ophthalmol*, 1980; 87:1189-1200.
Encyclopedia of Electronics, 2d Ed., Stan Gibilisco and Neil Sclater, Co-Editors-in-Chief, pp. 640-645 (1990).
Fenwick, P.B.C., Stone, S.A., Bushman, J., Enderby, D., "Changes in the Pattern Reversal Visual Evoked Potential as a Function of Inspired Nitrous Oxide Concentration," *Electroencephalogr Clin Neurophysiol*, 1984; 57178-183.
John B. Flynn, et al. "Total Active Area Silicon Photodiode Array", 3 pages (1964).
Graeme, J., "Position-Sensing Photodiode Amplifiers," Ch. 10, 12 pages.
Granit, R., Helme, T., "Changes in Retinal Excitability Due to Polarization and Some Observatios on the Relation Between the Processes in Retina and Nerve," *J. Neurophysiol*, 1939; 2:556-565.
Hagins, W.A., Penn, R.D., Yoshikami, S., "Dark Current and Photocurrent in Retinal Rods," *Biophys J.*, 1970; 10:380-412.
Hergert, Karl, "Detectors: Expanded Photodetector Choices Pose Challenges for Designers", The Photonics Design and Applications Handbook (1996).
Humayun, M.S., Propst, R.H., Hickinbotham, D., deJuan E., Jr., Dagnelie G., "Visual Sensations Produced by Electrical Stimulation of the Retinal Surface in Patients with Ed-Stage Retinities Pigmentosa (RP)," ARVO Abstracts, *Invest Ophthalmol Vis. Sci.*, 1993; 34 (Suppl):835.
Humayun, M., Propst R., De Juan, E., et al., "Bipolar Surface Electrical Stimulation of the Vertebrate Retina," *Arch Ophthalmol*, 1994; 112:110-116.
Kataoka, "An Attempt Towards an Artificial Retina: 3-D IC Technology for an Intelligent Image Sensor," *Transducers*

'85: International Conference on Solid-State Sensors and Actuators 1985, pp. 440-442.

Knighton, R.W., "An Electrically Evoked Slow Potential of the Frog's Retina. I. Properties of Response," J. Neurophysiol, 1975; 38-185-197.

Melen, et al., "A Transparent Electrode CCD Image Sensor for a Reading Aid for the Blind," IEEE Jounal of Solid-State Circuits, vol. SC-9, No. 2, Apr. 1974, pp. 41-48.

Narayanan, M.V., Rizzo, J.F., Edell, D., et al., "Development of a Silicon Retinal Implant: Cortical Evoked Potentials Following Focal Stimulation of the Rabbit Retina with Light and Electricity," ARVO Abstracts, Invest Opthalmol Vis Sci., 1994; 35(Suppl): 1380.

Pagon, R.A., "Retinitis Pigmentosa," Surv Ophthalmol., 1988; 33:137-177.

Paton, D., Goldberg, M.F., Management of Ocular Injuries, Philadelphia, W.B. Saunders Co., 1976; 134-135.

The Penguin Dictionary of Electronics, Editor: Valerie Illingworth, Carol Young Market House Books Ltd., pp. 410-413 (1988).

Potts, A.M., Inoue J., Buffum D., "The Electrically Evoked Response of the Visual System (EER)," Invest Ophthalmol Vis Sci., 1968; 7:269-278.

Robblee, Lois S., Electrochemical Guidelines for Selection of Protocols and Electrode Materials for Neural Stimulation, ch. 2, Renner Learning Resource Center, undated.

Rovamo, J., Virsu, A., "An Estimation and Application of the Human Cortical Magnification Factor," Exp Brain Res., 1979; 37:495-510.

Rubin, M.L., Optics for Clinicians, Gainsville, TRIAD Scientific Publishers, 1974; 119-123.

Shannon, R.V., "A Model of Safe Levels for Electrical Stimulation," IEEE Tams Biomed Eng., 1992; 39:424-426.

Smith, J., "Creating a Bionic Eye", ABC News, Nov. 5, 1998, 3 pp.

Stone, J.L., Barlow, W.E., Humayun, M.S., deJuan, E., Jr., Milam, A.H., "Morphometric Analysis of Macular Photoreceptor and Ganglion Cells in Retinas with Retinitis Pigmentosa," Arch Ophthalmol, 1992; 110:1634-1639.

Sze, S.M., "Physics of Semiconductor Devices", $2^{nd}$ Ed., A Wiley-Interscience Publication, John Wiley & Sons, undated.

Tasman, E., ed. Duane's Foundations of Clinical Ophthamology, vol. 3, Philadelphia, Lippincott, 1992; chapter 13:20-25, chapter 60:1-112.

Terr, L.I., Linthicum, F.H., House, W.F., "Histopathologic Study of the Cochlear Nuclei After 10 Years of Electrical Stimulation of the Human Cochlea," Am J Otol., 1988; 9:1-7.

Tomita, T., "Electrical Activity of Vertebrate Photoreceptor," Q Rev. Biophys., 1970; 3:179-222.

Zrenner, Dr. Eberhart, The Development of Subretinal Microphotodiodes for Replacement of Degenerated Photoreceptors, Ophthalmic Res. pp. 269-280 (1997).

Miyoshi, Tomomitsu, Morimoto Takeshi, Fujikado, Takashi, Tano, Yasuo and Fukuda, Yutaka, "Inhibition of Neuronal Death of Retinal Ganglion Cell by Nerve Activation Using Electrical Stimulation", Vision Forum, $5^{th}$ Annual Meeting, The Kitakyushu Science and Research Park Open Commemorative Project Assent: "Symposium of Visual Neuroscience and IT".

Morimoto Takeshi, Miyoshi, Tomomitsu, Fujikado, Takashi, Tano, Yasuo and Fukuda, Yutaka, "Electrical stimulation enhances the survival of axotomized retinal ganglion cells in vivo", NEUROREPORT, vol. 13, No. 2, Feb. 11, 2002, pp. 227-230 and Erratum.

Yokoyama, Akiko, Oshitari, Toshiyuki, Negishi, Hisanari, Dezawa, Mari, Mizota, Atushi and Adachi-Usami, Emiko, "Protection of Retinal Ganglion Cells from Ischemia-Reperfusion Injury to Electrically Applied Hsp27," Investigative Ophthalmology & Visual Science, Dec. 2001, vol. 42, No. 13, pp. 3283-3286.

* cited by examiner

ARTIFICIAL RETINA DEVICE WITH STIMULATING AND GROUND RETURN ELECTRODES DISPOSED ON OPPOSITE SIDES OF THE NEURORETINA AND METHOD OF ATTACHMENT

This is a continuation of application Ser. No. 09/564,841, filed May 4, 2000, now U.S. Pat. No. 6,427,087.

FIELD OF THE INVENTION

The present invention is generally directed to medical devices. More particularly, the present invention is directed to an artificial retina medical device and method to more efficiently stimulate electrically and with higher resolution, neuroretinal cells in partially damaged retinas to produce artificial vision. The invention provides improved efficiency and resolution of the device by using transretinal electrical current stimulation provided by stimulation and ground return electrodes that are disposed on opposite sides of the neuroretina.

BACKGROUND

A variety of retina diseases cause vision loss or blindness by destruction of the vascular layers of the eye that include the choroid and choriocapillaris, and the outer retinal layers that include Bruch's membrane and retinal pigment epithelium. Loss of these layers is often accompanied by degeneration of the outer portion of the neuroretina, typically the photo-receptor layer. Variable sparing may occur of the remaining neuroretina composed of the outer nuclear, outer plexiform, inner nuclear, inner plexiform, ganglion cell and nerve fiber layers.

Known prior efforts to produce vision by retinal electrical stimulation used arrays of stimulating electrodes with their ground return electrode or electrodes disposed either entirely on the epiretinal or the subretinal side of the neuroretina. Placement of stimulating and ground return electrodes together in this fashion resulted in inefficient stimulation of the neuroretina because the electrical field was not forced directly through the neuroretina. Resolution was also degraded because of diffuse spreading of each stimulating electrode's electrical field.

BRIEF SUMMARY OF THE PREFERRED EMBODIMENTS

The artificial retina device of this invention is preferably composed of two basic units, the stimulating electrode unit and the ground return electrode unit. In one embodiment, the two units are physically and electrically continuous, or physically and electrically connected by an insulated tail-like conductor that in some embodiments supports, positions, and aligns the two units on opposite sides of the neuroretina relative to each other. The stimulating electrode unit is, for example, a silicon disk 3 mm in diameter and 25 microns thick, and is comprised of separated stimulating microelectrode subunits. Preferably, the stimulating electrode unit has a ground return electrode unit extending from one edge, comprised of a silicon tail with an insulated conductor leading to the ground return electrode at its tip. The stimulating microelectrode subunits of the stimulating electrode units deliver current generated by one or more microphotodiodes connected, for example, in series and fabricated within the subunit. The preferred number of microphotodiodes per subunit is one.

In other embodiments, each microelectrode subunit is preferably fabricated on a node of a disk-shaped silicon web, the subunits separated by open areas of the web. The open areas of the web allow nourishment and oxygen from the outer retinal circulation to diffuse into the neuroretina.

In the preferred embodiment, on the backside of the stimulating electrode unit, i.e. the side opposite the incident light side, an insulated common conductor is constructed and arranged to electrically ground the microelectrode subunits. The common ground conductor preferably continues along the length of the ground return electrode unit and terminates in an exposed ground return electrode at or near the tip of the ground return electrode unit, and disposed in the vitreous cavity. The exposed ground return electrode tip in the vitreous cavity allows the electrical field generated by the microelectrode subunits in the subretinal space to transretinally stimulate the neuroretina.

In a second embodiment, an additional tail with an embedded conductor and an electrode tip is connected to the ground electrode tip of the ground electrode unit to extend the location of the ground electrode further into the vitreous cavity.

In a third embodiment, the conductor of the ground electrode unit is electrically connected with an additional bias photodiode or photodiodes to increase the voltage and current generated by the device. In this latter case, the ground electrode of the device is preferably disposed on the additional bias photodiode or photodiodes disposed in the vitreous cavity.

In a fourth embodiment, the bias photodiode or photodiodes are placed in the lens capsular bag of the eye after surgical removal of the lens nucleus and cortical material.

BRIEF DESCRIPTION OF THE DRAWINGS

Other features and advantages of the invention will be apparent to those skilled in the art with reference to the detailed description and the drawings, of which.

DETAILED DESCRIPTION OF THE PREFERRED EMBODIMENTS

Figures 1A, 1B:
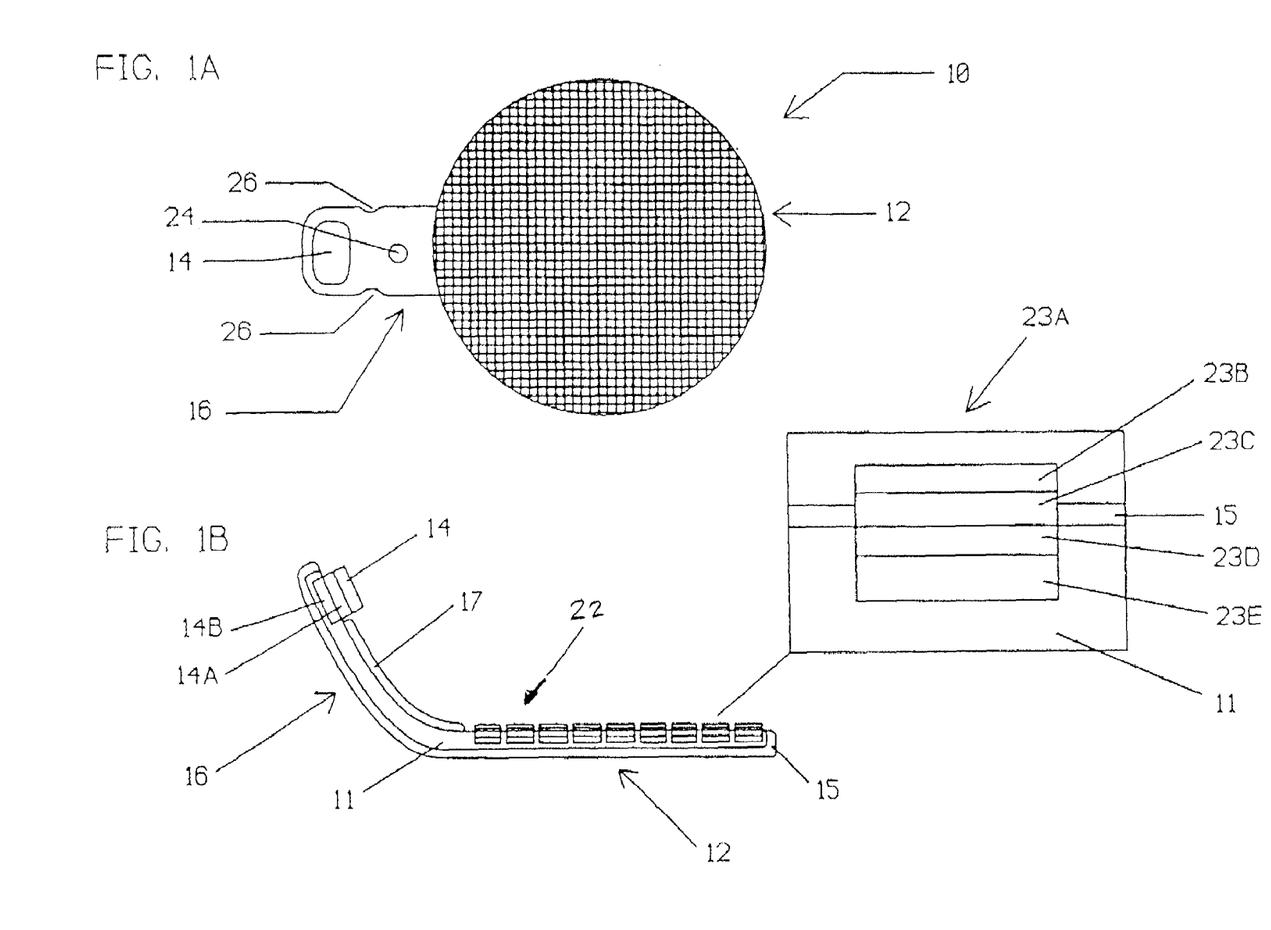
FIG. 1A is a plan view of a preferred embodiment showing the stimulating electrode unit and the ground return electrode unit.
FIG. 1B is a side view of FIG. 1A showing the stimulating electrode unit and the ground return electrode unit.

Referring to the drawings, as shown in FIGS. 1A and 1B, the preferred embodiment of retinal device 10 has a stimulating electrode unit 12 and a curved ground return electrode unit 16 configured for implantation into an eye such that the retinal device may be positioned completely inside the eye and stimulate opposite or substantially opposite sides of the neuroretina. The two components 12 and 16 are preferably physically fabricated on a single thin silicon chip substrate 11, but may be fabricated separately and then joined together. The stimulating electrode unit 12 includes an array of stimulating electrode subunits 22 each composed of one or more electrical sources such as a photodetector or photodetectors. In a preferred embodiment, the photodetectors may be implemented as microphotodiodes 23a electrically connected, for example, in series.

A stimulating electrode 23b contacts at least one of individual cells, groups of cells, portions of cells and nerve fibers of the neuroretina. The ground return electrode 14 is preferably disposed at or near the tip of the ground return electrode unit 16. The stimulating electrode 23b and ground return electrode 14 are disposed on opposite sides of a neuroretina, or if the neuroretina is partially missing or damaged, then on opposite sides of the remainder of the neuroretina. In a preferred embodiment, the stimulating electrode 23b is disposed in a subretinal space of the neuroretina and the ground return electrode 14 is disposed on an epiretinal side of the neuroretina. In another embodiment, the positions are reversed, with the ground return electrode 14 being disposed in the subretinal space of the neuroretina and the stimulating electrode 23b being disposed on the epiretinal side of the neuroretina.

Also as shown in FIGS. 1A and 1B, exemplary components of the preferred embodiment of retinal device 10 includes the thin silicon substrate 11, stimulating electrode unit 12, stimulating electrode subunits 22, microphotodiodes 23a electrically connected, for example, in series, within stimulating electrode subunits 22 and an iridium/iridium oxide stimulating electrode 23b of stimulating electrode subunits 22. The microphotodiodes 23a or other electrical source preferably provides stimulation to the neuroretina from the subretinal and vitreous cavity sides of the eye. Alternatively, the electrical source could provide stimulation from outside the eye in response to incident light. For example, the electrical source could send signals proportional to sensed incident light via hardwiring into the subretinal space and vitreous cavity of the eye. In another embodiment, the electrical source could transmit a signal in a wireless fashion to the eye using, for example, radio frequency (RF) to send signals to a coil located in the eye that is in communication with the stimulation and ground electrodes. Other known mechanisms may also be used for providing electrical energy to the eye in response to incident light.

Also included with the ground return electrode unit 16 is a silicon nitrite stress layer 17 that preferably shapes the ground return electrode unit 16 in a generally curved shape to direct the ground return electrode unit 16 into the vitreous cavity. Although a curve directs the ground electrode unit 16 into the vitreous cavity, other shapes could be used, such as an angled ground electrode, to perform the same function, but may be more difficult to fabricate. The ground return electrode 14 is preferably produced of an iridium/iridium oxide and includes a titanium adhesion layer 14a and a P+ tub 14b disposed under a titanium adhesion layer 14a to allow electrical contact with the doped silicon substrate 11. The retinal device 10 also preferably includes a silicon dioxide layer 15 that insulates the stimulating electrode unit 12 and ground return electrode unit 16.

As shown in FIGS. 1A and 1B, the stimulating electrode unit 12 includes a plurality of stimulation electrode subunits 22 having one or more microphotodiodes 23a electrically connected, for example, in series within each electrode subunit 22. The preferred number of microphotodiodes 23a is one unit per microelectrode subunit 22. The layers of the microphotodiode are, for example, from the incident light surface, the iridium/iridium oxide electrode 23b, titanium adhesion layer 23c, N+ tub 23d, intrinsic layer 23e and the silicon substrate 11. Those skilled in the art will appreciate that other arrangements could be used where the microelectrode subunits are subunits capable of generating electrical current.

Also shown in FIGS. 1A and 1B, the ground return electrode unit 16 preferably includes a positioning hole 24 that allows the retinal device 10 to be positioned with instruments during surgery. The ground return electrode unit 16 in another embodiment includes notches 26 that allow a secure fit for attachments that have corresponding protrusions that fit into the notches 26, as described in more detail below.

Figure 2A:
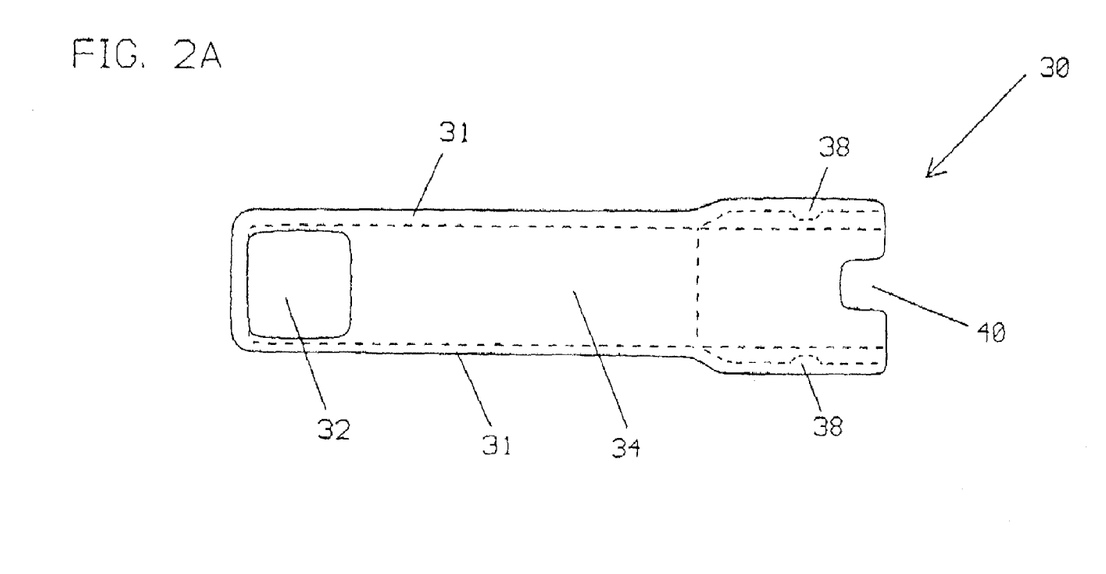
FIG. 2A is a plan view of the tail extension of the preferred embodiments, that physically and electrically couples to the ground return electrode unit of FIGS. 1A and 1B to extend the location of the ground return electrode further into the vitreous cavity of the eye.
Figure 2B:
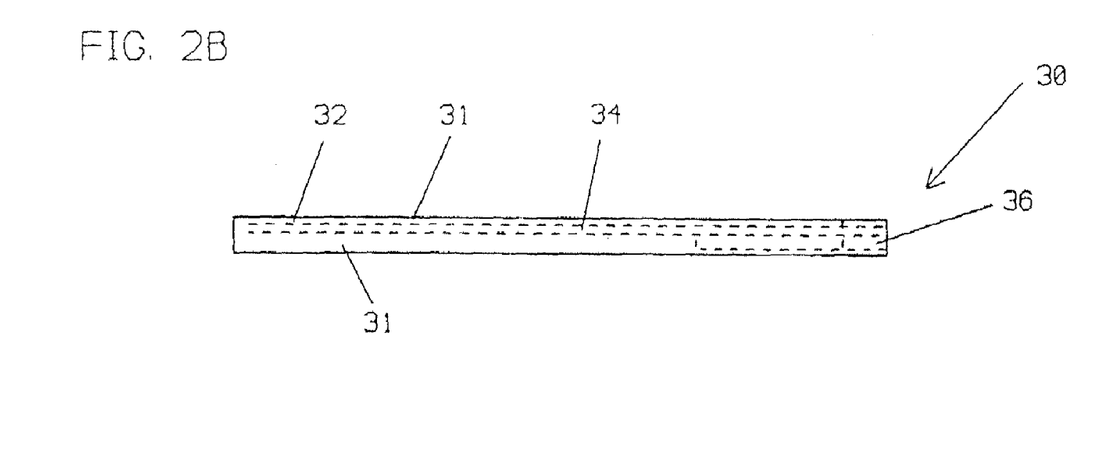
FIG. 2B is a cross-sectional view of the tail extension of the preferred embodiments.

As shown in FIGS. 2A and 2B, a tail extension 30 is disclosed for attachment to the ground return electrode unit 16 (shown in FIGS. 1A and 1B) to extend the electrical termination of the ground return electrode 14 (shown in FIGS. 1A and 1B), for example, further into the vitreous cavity. Further extension of the ground electrode into the vitreous cavity may be required to diminish undesirable skewing of the electric field that travels from the stimulating towards the ground electrode. Such a skewed electric field is less efficient in stimulating the neuroretina compared to an electrical field that is arranged in a direction perpendicular to the neuroretinal surface.

FIG. 2A is a plan view and FIG. 2B is a side view of the tail extension 30. The tail extension attachment 30 is constructed of a biocompatible material 31, such as Parylene or a similar biocompatible material and is preferably manufactured with a curve. The tail extension attachment 30 also includes an embedded conductor 34, insulated by the surrounding material 31, terminating in a tail extension ground return electrode 32 at or near an end of the tail extension attachment 30, preferably to locate the electrode as far into the vitreous cavity as possible. The conductor 34 of the tail extension attachment 30 is designed to electrically contact the ground return electrode 14 when the tail extension attachment 30 is attached to the ground return electrode unit 16 (shown in FIGS. 1A and 1B). The tail extension ground electrode 32 is preferably constructed of iridium/iridium oxide, or other suitable electrode material.

Also referring to FIGS. 1A and 1B, the tail extension attachment 30 has a pocket 36 that fits over the ground electrode unit 16 to establish electrical contact with the ground return electrode 14. Inside the pocket 36 are protrusions 38, which fit into the notches 26 of the ground return electrode unit 16. The protrusions 38 are preferably constructed of a biocompatible material, such as Parylene, or a similar biocompatible material. The tail extension attachment 30 includes a slot 40 that allows the positioning hole 24 of the ground return electrode unit 16 to be access by an instrument (not shown).

Figure 3:
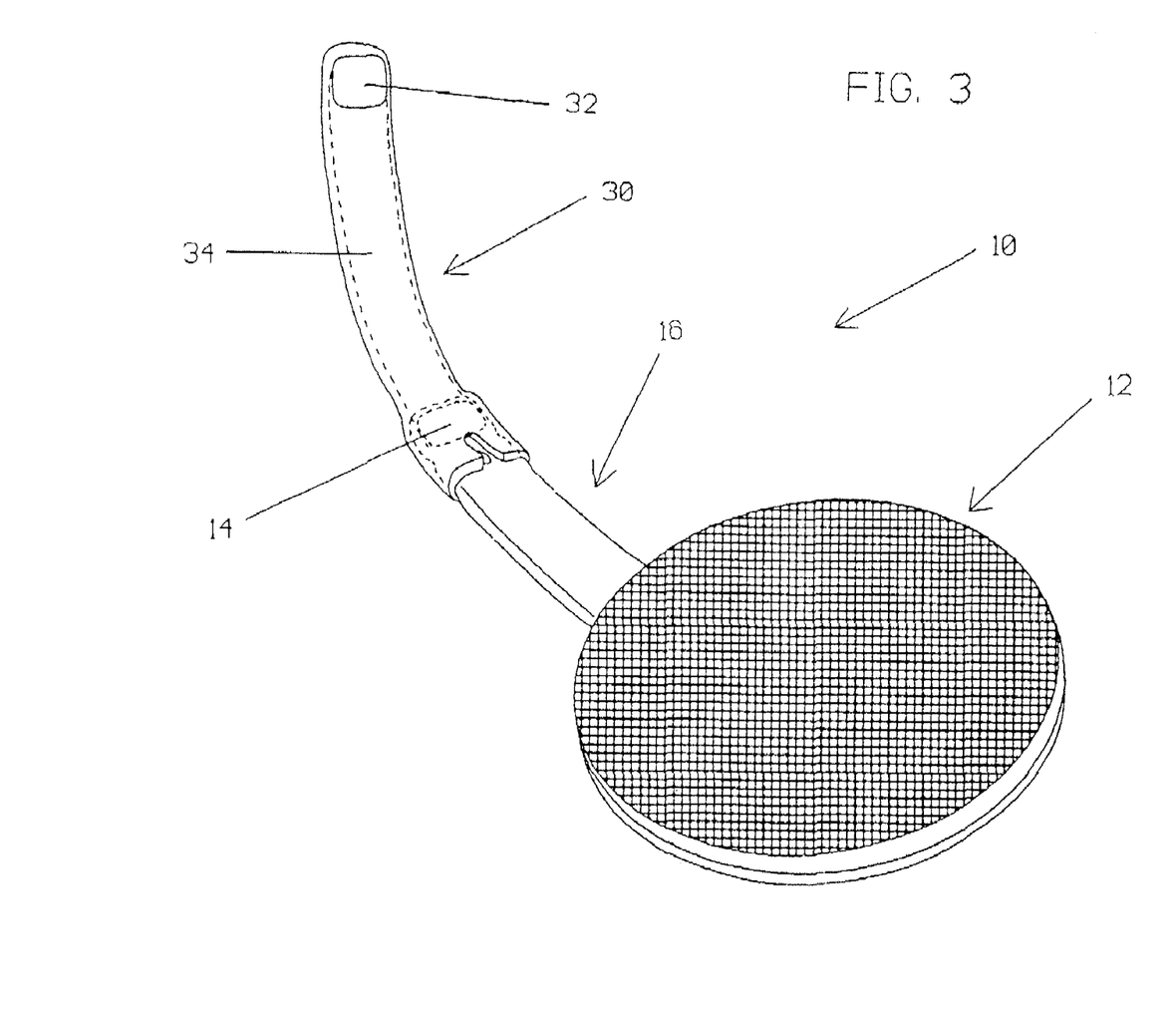
FIG. 3 is a perspective view showing the tail extension of FIGS. 2A and 2B attached to the ground return electrode unit of FIGS. 1A and 1B.

FIG. 3 is a perspective view showing the tail extension 30 (shown in FIGS. 2A and 2B) electrically attached with the ground return electrode unit 16 of the retinal device 10. The conductor 34 of the tail extension 30 contacts the ground return electrode 14 of the ground return electrode unit 16. The tail extension 30 is preferably curved to position its ground return electrode 32 into the vitreous cavity of the eye. Those skilled in the art will appreciate that other shapes of the tail extension could be used as long as the shape positions the ground return electrode into the vitreous of the eye. The stimulating electrode unit 12 is also shown.

Figure 4:
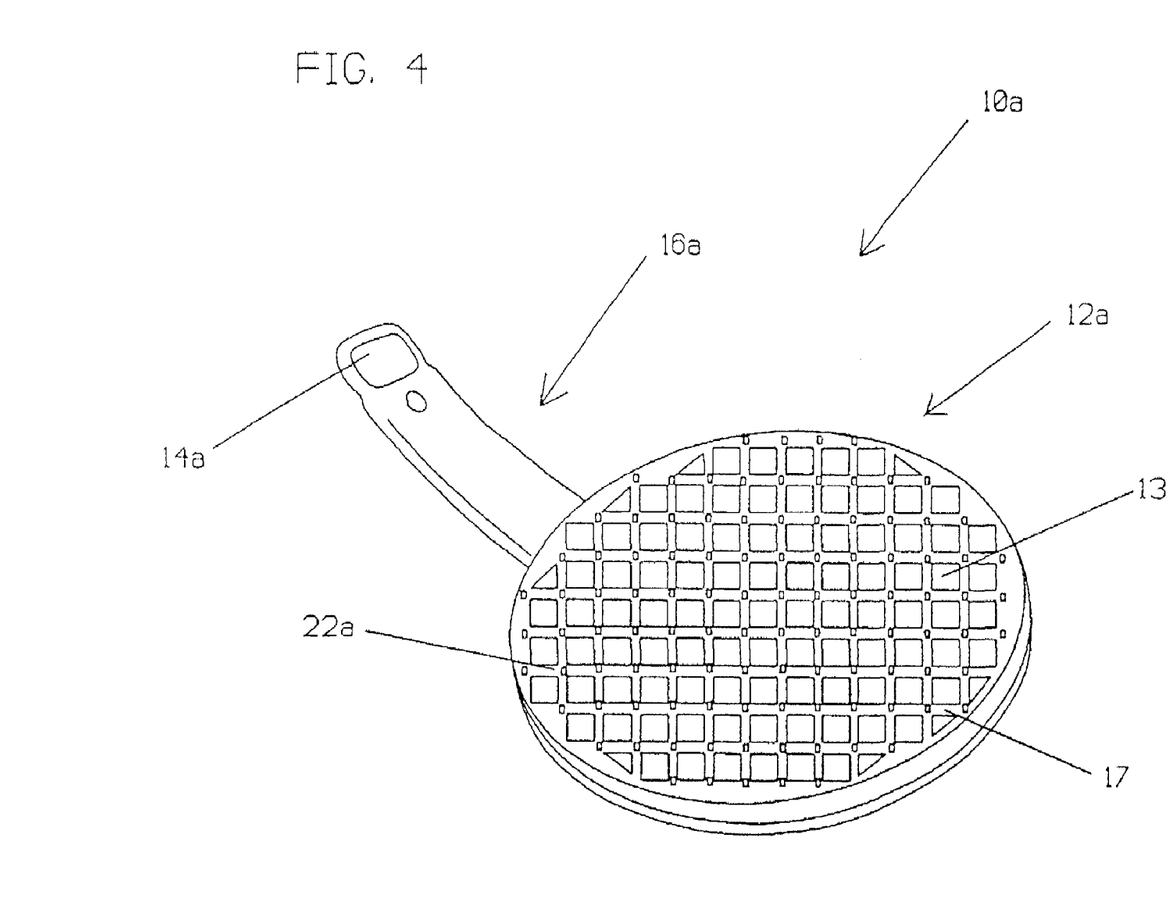
FIG. 4 is a perspective view of another embodiment, showing the stimulating electrode unit fabricated as a circular silicon web to allow nourishment to flow between the choroid and the neuroretina, and the stimulating electrode subunits fabricated at the intersecting nodes of the web.

FIG. 4 is a perspective view of another embodiment of the retinal device 10 shown in FIGS. 1A and 1B. Like components are labeled using the same reference numerals followed by a letter. Alternative embodiment retinal device 10a is similar to the preferred embodiment retinal device 10 shown in FIGS. 1A and 1B, except that the stimulating electrode unit 12a is fabricated as a disk-shaped web 17 to allow nourishment to flow between the choroid and the neuroretina, and the stimulating electrode subunits 22a are fabricated at the intersecting nodes of the web 17. Preferably, the web is manufactured of silicon and can be perforated. The alternative embodiment retinal device 10a is thus similar to the preferred embodiment retinal device 10 with the addition of fabricated nutrient openings 13.

Figure 4A:
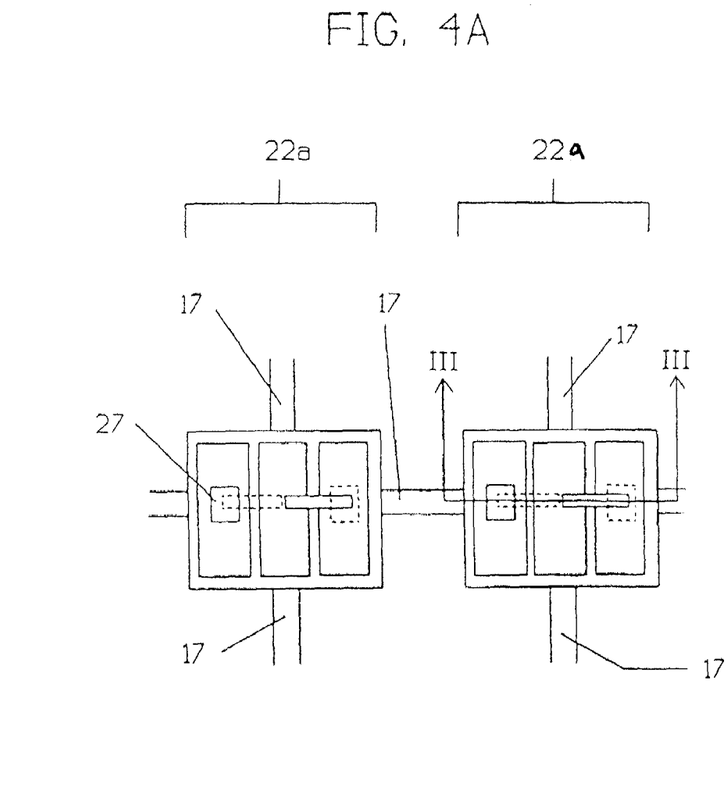
FIGS. 4A and 4B are magnified plan and sectional views respectively of the embodiment of FIG. 4 where the stimulating electrode subunits of the stimulating electrode unit are each comprised of three microphotodiodes electrically connected in series to increase the voltage output of each stimulating electrode subunit.
Figure 4B:
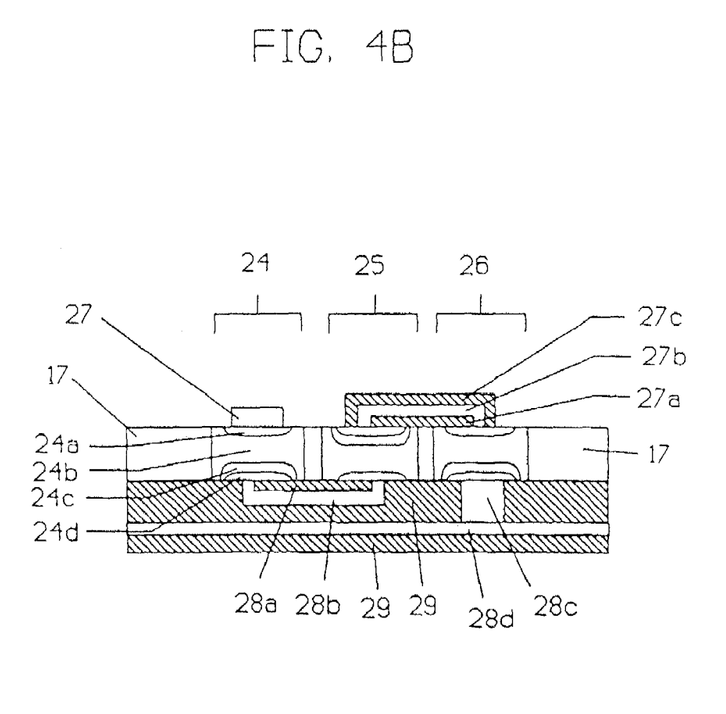

FIG. 4A is a magnified plan view, and FIG. 4B is sectional view taken through section III—III of FIG. 4A of an alternative embodiment of the retinal device 10a shown in FIG. 4. The stimulating electrode subunits 22a of the stimulating electrode unit 12a shown in FIG. 4 are each comprised of first, second, and third microphotodiodes 24, 25, 26 electrically connected, for example, in series within stimulating electrode subunit 22a to increase the output voltage of each stimulating electrode subunit 22a. The stimulating electrode subunits 22a contact a common ground conductor 28d via a contact pad 28c.

Preferably the common ground conductor 28d and contact pad 28c are insulated during fabrication, for example, by silicon dioxide 29 deposition. For clarity purposes, preferably only the layers of one of the microphotodiodes connected electrically in series is labeled; they are the N+ layer 24a, the N type silicon substrate 24b, the intrinsic layer 24c, and the P+ layer 24d. Conductors 27b, 28b are preferably deposited over insulating layers of silicon dioxide 27a, 28a to electrically connect the adjacent microphotodiodes 24, 25, 26. An insulating layer of silicon dioxide 27c covers conductor 27b. The stimulating electrode 27 of each stimulating electrode subunit 22a is preferably fabricated from iridium/iridium oxide deposited over a titanium adhesion layer. Those skilled in the art will appreciate that other electrode materials, for example, noble metals like platinum and tantalum, may be used. The common ground conductor 28d of the stimulating electrode subunits 22a terminates electrically, for example, at or near the ground return electrode 14a of the ground return electrode unit 16a, shown in FIG. 4.

Figure 5:
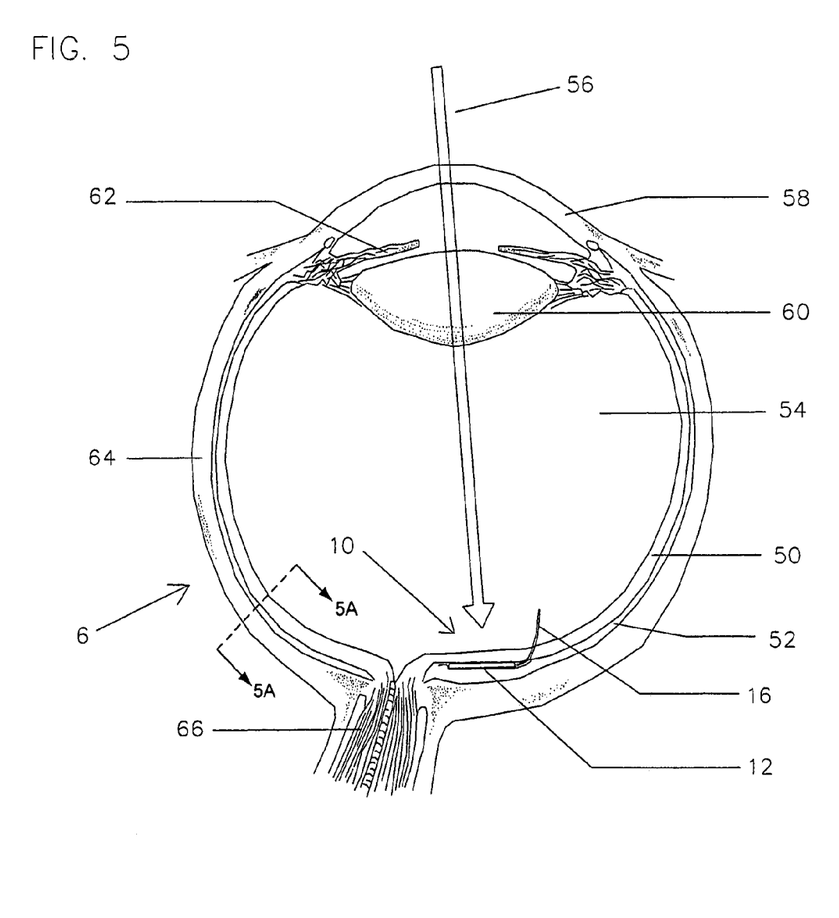
FIG. 5 is a cross-sectional view of FIGS. 1A and 1B, in the eye with a stimulating electrode unit in the subretinal space and a ground return electrode of the ground return electrode unit exposed in the vitreous cavity.
Figure 5A:
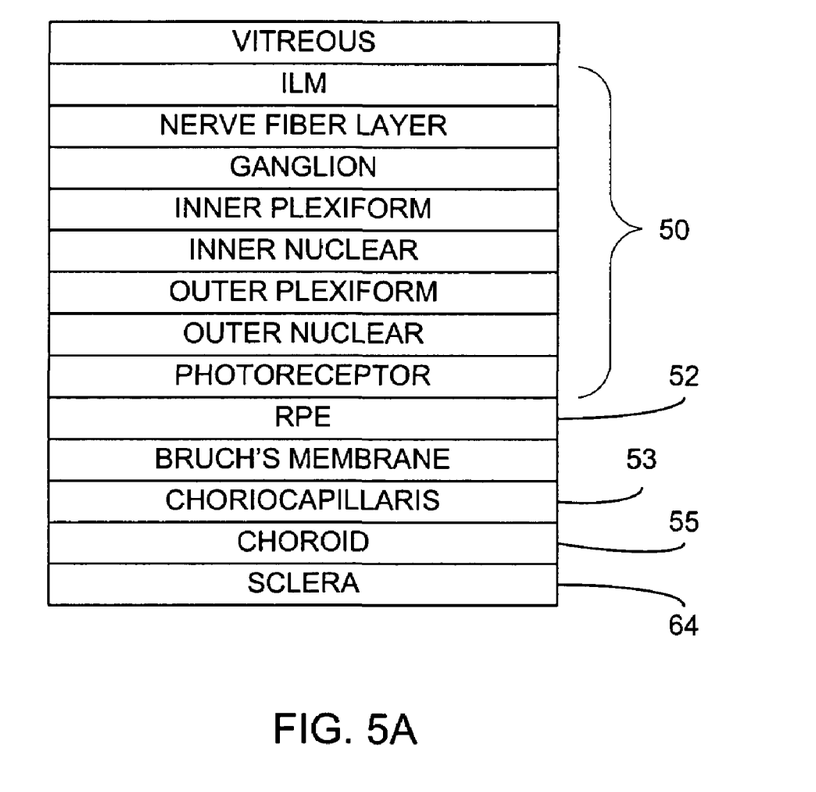
FIG. 5A is a cross-sectional view of the eye of FIG. 5 taken along line 5A—5A.

FIG. 5 is a cross-sectional view showing the preferred embodiment retinal device 10 of FIGS. 1A and 1B implanted in the eye 6 with the stimulating electrode unit 12 disposed in the subretinal space between the neuroretina 50 and the retinal pigment epithelium 52, and the ground return electrode unit 16 in the vitreous cavity 54. Light images 56 enter the eye 6 through the cornea 58 and lens 60 and are focused onto the stimulating electrode unit 12. Patterned electrical stimuli are then generated by the microphotodiodes of the electrode subunits 22 (FIG. 1A) that stimulate the overlying neuroretina 50 in the pattern of the image. For purposes of reference, other structures of the eye 6 that are shown are an iris 62, a sclera 64 and an optic nerve 66. FIG. 5A illustrates a more detailed partial cross-sectional view of the eye of FIG. 5 identifying additional layers of the eye such as Bruch's membrane, the choriocapillaris, and several layers of the neuroretina such as the outer nuclear, outer plexiform, inner nuclear, inner plexiform, ganglion cell and nerve fiber layers. In other embodiments, the ground return electrode may be adapted to be disposed between the choriocapillaris 53 and the retinal pigment epithelium 52, between the sclera 64 and the choroid 55, and on the sclera surface on the outside of the eye. In yet other embodiments, the stimulating electrode may be adapted to be disposed between the choriocapillaris 53 and the retinal pigment epithelium 52, between the sclera 64 and the choroid 55, and on the sclera surface on the outside of the eye.

Figure 6:
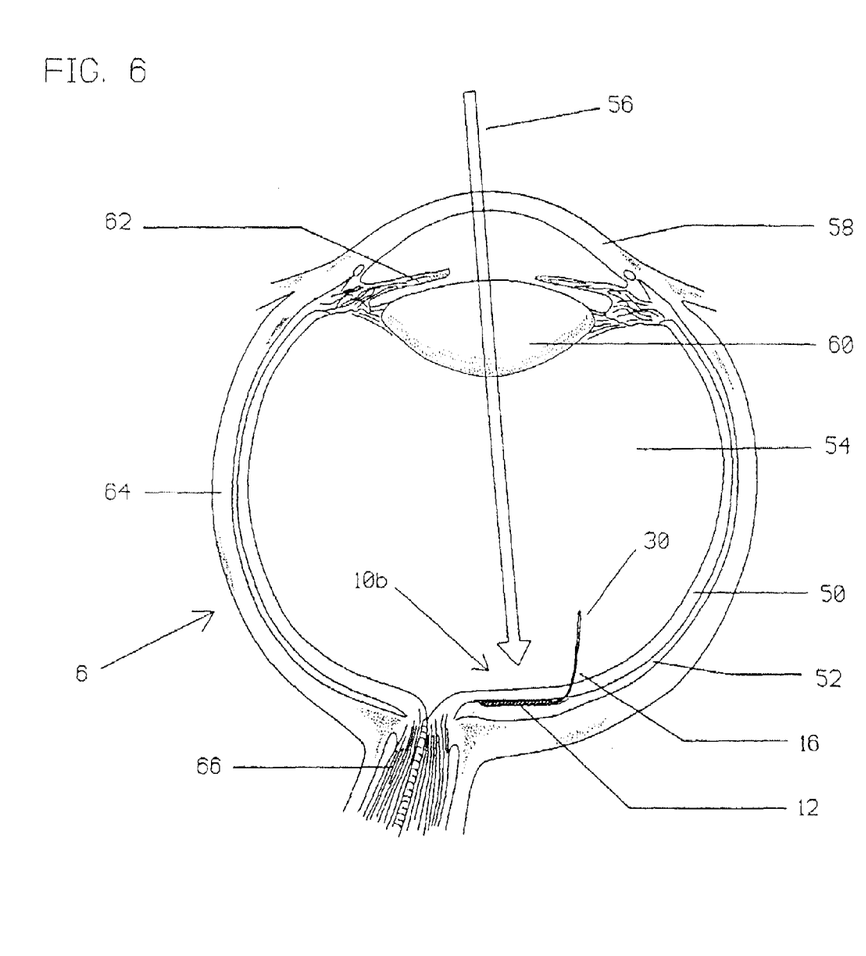
FIG. 6 is a cross-sectional view of the device of FIG. 5 with the attached tail extension of FIGS. 2A and 2B.

FIG. 6 shows a cross-sectional view of an alternate embodiment retinal device 10b, including the preferred embodiment retinal device 10 as described in FIGS. 1A and 1B and other features. The alternate embodiment retinal device 10b includes the stimulating electrode unit 12 disposed in the subretinal space between the neuroretina 50 and the retinal pigment epithelium 52, and the ground return electrode unit 16 in the vitreous cavity 54, with attached tail extension 30 of FIGS. 2A and 2B. A purpose of the tail extension 30 is to electrically extend the location of the ground return electrode further into the vitreous cavity 54 to prevent skewing of the transretinal electric field between the stimulating electrode unit 12 and the ground return electrode unit 16 as the electric field traverses through the neuroretina 50. A non-skewed electrical field that is perpendicular to the neuroretina vitreous-facing surface efficiently stimulates remaining neuroretinal cells. For reference purposes, other items and structures of the eye that are shown are the cornea 58, iris 62, lens 60, sclera 64, optic nerve 66 and the incident light images 56.

Figure 7:
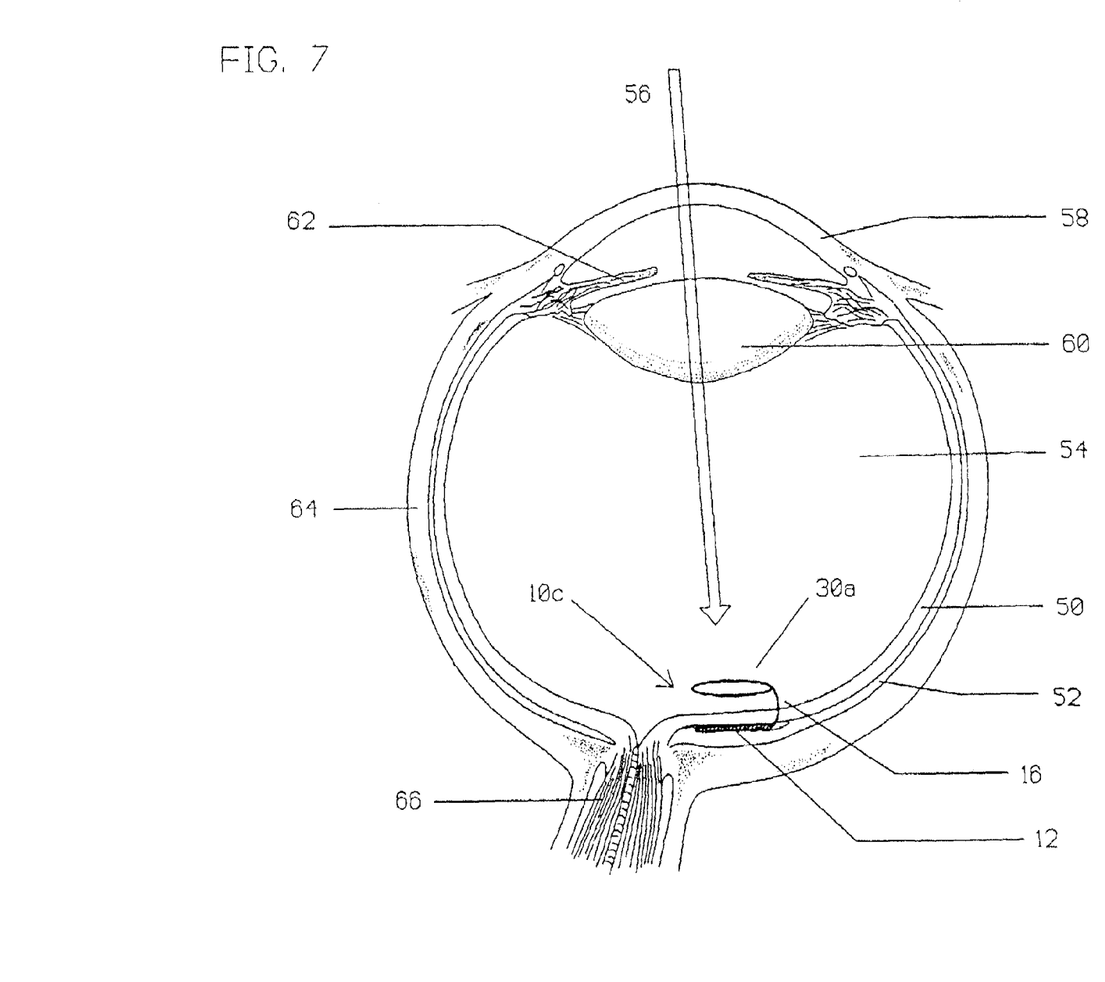
FIG. 7 is a cross-sectional view of another embodiment, showing the device of FIGS. 1A and 1B with an electrode stimulating unit implanted in the subretinal space and a ground return electrode loop of the ground return electrode unit disposed in the vitreous cavity.

FIG. 7 shows a cross-sectional view of another embodiment of the retinal device 10c including the preferred embodiment retinal device 10 as described in FIGS. 1A and 1B and other features. The stimulating electrode unit 12 is disposed in the subretinal space between the neuroretina 50 and the retinal pigment epithelium 52, and the ground return electrode unit 16 is disposed in the vitreous cavity 54, including a tail extension 30a that has a generally looped ground electrode. Although the stimulating electrode unit 12 is preferably positioned in the subretinal space with the ground return electrode unit 16 positioned in the vitreous cavity, in other embodiments the positioning of the stimulating electrode unit 12 and ground electrode unit 16 may be reversed.

A purpose of the loop electrode of the tail extension 30a is to electrically extend the location of the ground return electrode further into the vitreous cavity 54 and in an even manner. An evenly disposed ground electrode in the vitreous cavity relative to the subretinal stimulating electrode array aids the maintenance of a tranretinal stimulating electrical field in a perpendicular direction relative to the neuroretinal surface. Such an alignment of the electrical field relative to the neuroretinal surface efficiently stimulates the neuroretina, as compared to, for example, a transretinal electrical field that is skewed to the neuroretinal surface. For purposes of reference, other items and structures of the eye that are shown are the cornea 58, iris 62, lens 60, sclera 64, optic nerve 66 and the incident light images 56.

Figure 8:
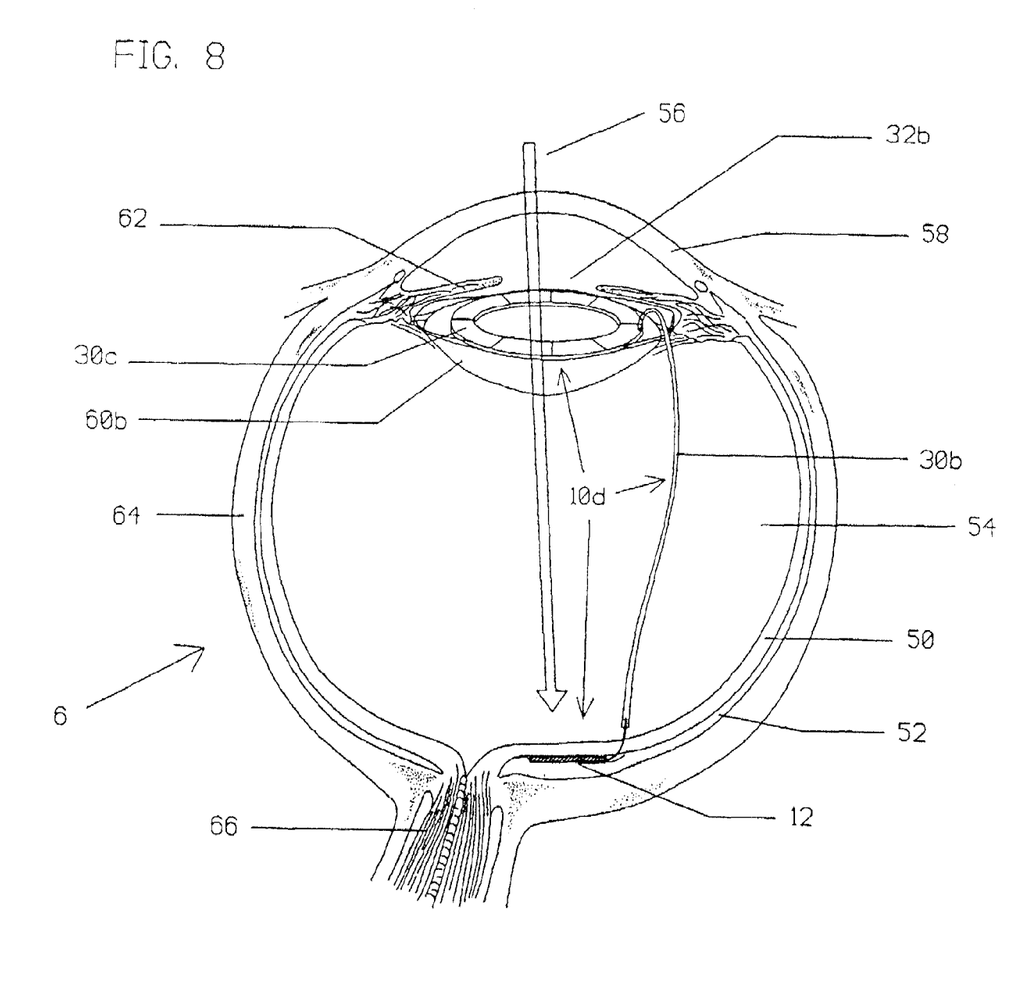
FIG. 8 is a cross-sectional view of another preferred embodiment, showing the device of FIGS. 1A and 1B with a stimulating electrode unit implanted in the subretinal space and a tail extension electrically connecting to a bias photodiode disposed in the lens capsule of the eye, the bias photodiode containing the extended location of the ground return electrode, and the bias photodiode providing additional voltage and/or current to the electrode stimulating unit in the subretinal space.

FIG. 8 shows a cross-sectional view of yet another embodiment retinal device 10d including the preferred embodiment retinal device 10 as described in FIGS. 1A and 1B, including an attached tail extension 30b. The tail extension electrically connects with at least one bias photodiode 30c disposed in the lens capsule 60b of the eye 6, the bias photodiode 30c containing the extended location of the ground return electrode 32b. The bias photodiode 30c provides additional voltage and/or current to the electrode stimulating unit 12 in the subretinal space. Additional stimulating voltage and the resulting current may be required to stimulate more severely damaged retinas compared to less severely damage retinas. The bias photodiode, which may also be a series of photodiodes 30c are electrically connected together in a series or parallel configuration, as is known in the art, to provide the increased voltage and/or current. For purposes of reference, other items and structures of the eye 6 that are shown are the cornea 58, iris 62, sclera 64, neuroretina 50, retinal pigment epithelium 52, optic nerve 66, and the incident light images 56.

Figure 9:
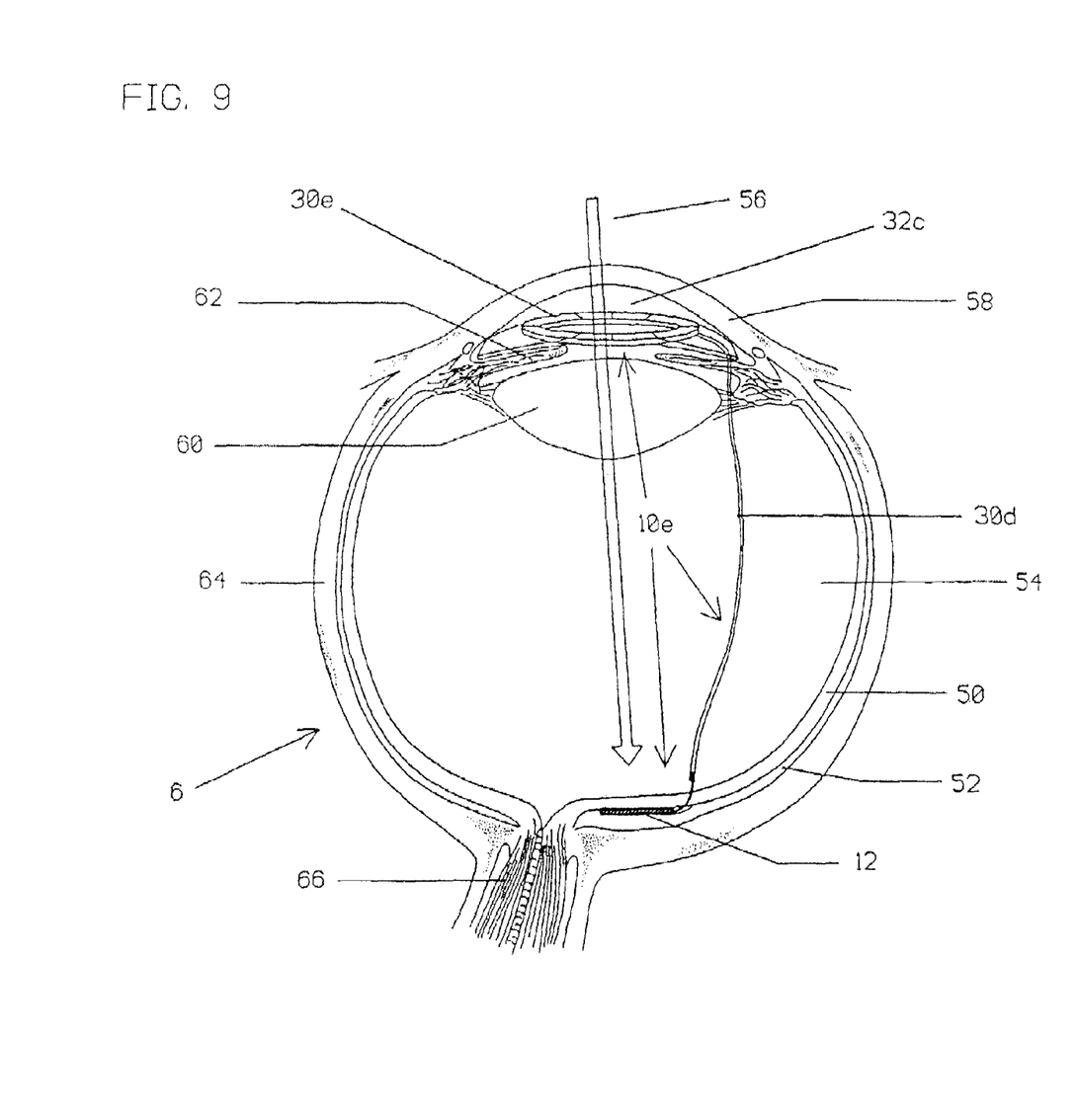
FIG. 9 is a cross-sectional view of another embodiment, showing the device of FIGS. 1A and 1B with its stimulating electrode unit implanted in the subretinal space and a tail extension electrically connecting to a bias photodiode disposed in front of the iris, in the anterior chamber of the eye, the bias photodiode containing the extended location of the ground return electrode, and the bias photodiode providing additional voltage and/or current to the electrode stimulating unit in the subretinal space.

FIG. 9 shows a cross-sectional view of yet another embodiment retinal device 10e including the preferred embodiment retinal device 10 as described in FIGS. 1A and 1B, and an attached tail extension 30d that electrically connects with at least one bias photodiode 30e preferably disposed in front of the iris 62 of the eye 6. The placement of at least one bias photodiode in this location allows all of the bias photodiode to be exposed to light, compared to a bias photodiode disposed behind the iris. The bias photodiode 30e contains the extended location of the ground return electrode 32c, and the bias photodiode or photodiodes 30e to provide additional voltage and/or current to the electrode stimulating unit 12 in the subretinal space. The bias photodiode or photodiodes 30e are electrically connected together in a series or parallel configuration to provide increased voltage and/or current, as is known in the art. For reference purposes, other items and structures of the eye 6 that are shown are the cornea 58, lens 60, sclera 64, neuroretina 50, retinal pigment epithelium 52 and optic nerve 66, and the incident light images 56.

It is to be understood that changes and modifications to the embodiments described above will be apparent to those skilled in the art, and are contemplated. It is therefore intended that the foregoing detailed description be regarded as illustrative rather than limiting, and that it be understood that it is the following claims, including all equivalents, that are intended to define the spirit and scope of this invention.

We claim:

1. An artificial retina device to electrically stimulate a neuroretina of an eye, the artificial retina device comprising:
   an electrical source;
   at least one stimulating electrode connected with the electrical source; and
   at least one ground return electrode connected with the electrical source, wherein the stimulating electrode and ground electrode are configured to direct an electrical field through the neuroretina, wherein the electrical field is substantially perpendicular to the neuroretina.

2. The device of claim 1 wherein the electrical source is a photodetector.

3. The device of claim 2 wherein the photodetector is a microphotodiode array.

4. The device of claim 1 wherein the stimulating electrode is positionable in a subretinal space of the neuroretina.

5. The device of claim 1 wherein the ground return electrode is positionable in an epiretinal side of the neuroretina.

6. The device of claim 1 wherein the at least one stimulating electrode comprises a plurality of stimulating electrodes configured in an array.

7. The device of claim 6 wherein the at least one stimulating electrode array is fabricated on a web.

8. The device of claim 7 wherein the web comprises silicon.

9. The device of claim 7 wherein the web comprises a biocompatible material.

10. The device of claim 6 wherein the electrical source comprises at least one photodetector, and wherein the at least one stimulating electrode of the stimulating electrode array receives at least one of voltage and current from the at least one photodetector.

11. The device of claim 10 wherein the at least one photodetector comprises a plurality of photodetectors, and wherein each of the plurality of photodetectors is disposed proximal to one another adjacent to the stimulating electrode.

12. The device of claim 11 wherein the plurality of photodetectors and stimulating electrode are adapted to be disposed on an epiretinal or subretinal side of the neuroretina, such that images focused into the eye will produce an area of stimulation.

13. The devices of claim 10 wherein at least one bias photodiode is electrically connected to the stimulating electrode array to provide at least one of additional voltage and current to the stimulating electrode array.

14. The device of claim 13 wherein the at least one bias photodiode is adapted to be disposed in at least one of a vitreous cavity posterior to a lens capsule, within the lens capsule, behind an iris and in front of the iris of the eye.

15. The device of claim 14 wherein at least one of additional voltage and current are provided to the stimulating electrodes by electrically connecting the at least one bias photodiode to at least one of the plurality of photodetectors.

16. The device of claim 10 wherein the at least one photodetector is adapted to be disposed in a subretinal space of the neuroretina.

17. The device of claim 1 wherein at least one ground return electrode is fabricated on a web.

18. The device of claim 17 wherein the web comprises silicon.

19. The device of claim 1 wherein the ground return electrode is adapted to be disposed in a vitreous cavity of the eye.

20. The device of claim 1 wherein the ground return electrode is adapted to be disposed within a lens capsule of the eye.

21. The device of claim 1 wherein the ground return electrode is adapted to be disposed in an anterior chamber of the eye.

22. The device of claim 1 wherein at least one of the at least one stimulating electrode contacts at least one of individual cells, groups of cells, portions of cells and nerve fibers of the neuroretina.

23. The device of claim 1 wherein at least one of the at least one stimulating electrode is adapted to be disposed close to but not touching an epiretinal side of the neuroretina.

24. The device of claim 1 wherein at least one of the at least one ground return electrode is adapted to be disposed between a choriocapillaris and a retinal pigment epithelium.

25. The device of claim 1 wherein at least one of the at least one ground return electrode is adapted to be disposed between a sclera and a choroid.

26. The device of claim 1 wherein at least one of the at least one ground return electrode is adapted to be disposed on a sclera surface on an outside of an eye.

27. The device of claim 1 wherein at least one of the at least one stimulating electrode and the at least one ground return electrode is adapted to be disposed on the epiretinal side of the neuroretina.

28. The device of claim 27 wherein at least one of the at least one ground return electrode is adapted to be disposed between a choriocapillaris and a retinal pigment epithelium.

29. The device of claim 27 wherein at least one of the at least one ground return electrode is adapted to be disposed between a sclera and a choroid.

30. The device of claim 27 wherein at least one of the at least one ground return electrode is adapted to be disposed on a sclera surface on an outside of an eye.

31. The device of claim 27 wherein at least one of the at least one stimulating electrode is adapted to be disposed between a choriocapillaris and a retinal pigment epithelium.

32. The device of claim 27 wherein at least one of the at least one stimulating electrode is adapted to be disposed between a sclera and a choroid.

33. The device of claim 27 wherein at least one of the at least one stimulating electrode is adapted to be disposed on a sclera surface that faces an outside of the eye.

34. The device of claim 1 wherein at least one of the at least one ground return electrode is adapted to be disposed in a subretinal space side of the neuroretina.

35. A method for using an artificial retina device, wherein the artificial retina device comprises an electrical source, and a stimulating electrode and a ground return electrode connected with the electrical source, to stimulate a neuroretina of an eye, the method comprising:
implanting the stimulating electrode on a first side of the neuroretina; and
implanting the ground return electrode relative to the stimulating electrode such that an electrical field generated by the electrical source is directed in a substantially perpendicular orientation through the neuroretina.

36. The method of claim 35 wherein the stimulating electrode is positionable in a subretinal space of the neuroretina.

37. The method of claim 35 wherein the ground return electrode is positionable on an epiretinal side of the neuroretina.

38. The method of claim 35 wherein the stimulating electrode comprises a plurality of stimulating electrodes configured in an array.

39. The method of claim 35 wherein the stimulating electrode is positionable on an epiretinal side of the neuroretina and the ground return electrode is positionable in a subretinal space of the neuroretina.

40. An artificial retina device to electrically stimulate a neuroretina of an eye, the artificial retina device comprising:
an electrical source;
a stimulating electrode connected with the electrical source; and
a ground return electrode connected with the electrical source, wherein the stimulating electrode and ground return electrode are configured to be disposed on opposite sides of the neuroretina.

41. The device of claim 40, wherein the ground return electrode is adapted to be disposed between a choriocapillaris and a retinal pigment epithelium.

42. The device of claim 40 wherein the ground return electrode is adapted to be disposed between a sclera and a choroid of the eye.

43. The device of claim 40 wherein the ground return electrode is adapted to be disposed on a sclera surface on an outside of the eye.

44. The device of claim 40 wherein the stimulating electrode is adapted to be in contact with an epiretinal side of the neuroretina.

45. The device of claims 40 wherein the stimulating electrode is adapted to be disposed between a choriocapillaris and a retinal pigment epithelium.

46. The device of claims 40 wherein the stimulating electrode is adapted to be disposed between a sclera and a choroid of the eye.

47. The device of claims 40 wherein the stimulating electrode is adapted to be disposed on a sclera surface on an outside of the eye.

48. An artificial retina device to electrically stimulate a neuroretina of an eye, the artificial retina device comprising:
an electrical source;
at least one stimulating electrode connected with the electrical source; and
at least one ground return electrode connected with the electrical source, wherein the at least one stimulating electrode and ground return electrode are configured to be disposed in contact with the eye on opposite sides of the neuroretina, wherein at least one of the at least one stimulating electrode and the at least one ground return electrode is adapted to be disposed on a sclera surface on an outside of the eye.

49. An artificial retina device to electrically stimulate a neuroretina of an eye, the artificial retina device comprising:
an electrical source;
a stimulating electrode connected with the electrical source; and
a ground return electrode connected with the electrical source, wherein the stimulating electrode and ground return electrode are configured to be disposed on opposite sides of the neuroretina, and wherein the stimulating electrode is adapted to be disposed within the eye.

50. The device of claim 49, wherein the stimulating electrode is adapted to be positioned within a vitreous cavity of the eye.

51. The device of claim 49, wherein the stimulating electrode is adapted to be in contact with an epiretinal surface of the eye.

52. The device of claim 49, wherein the stimulating electrode is adapted to be positioned in a subretinal space of the eye.

* * * * *